United States Patent [19]

Gilligan et al.

[11] Patent Number: 5,505,216

[45] Date of Patent: *Apr. 9, 1996

[54] THIN FLOSS BRUSH

[75] Inventors: Sean G. Gilligan, Kilcullen, Ireland; John A. Kaminski, Newark; Adrian Hart, Menlo Park, both of Calif.; Dermot T. Freeman, Killiney, Ireland; Patrick J. Hanley, S. San Francisco, Calif.; Jeffrey S. Meessmann, Iowa City; Larry J. Oliphant, Swisher, both of Iowa

[73] Assignee: Gillette Canada Inc., Kirkland, Canada

[*] Notice: The term of this patent shall not extend beyond the expiration date of Pat. No. 5,284,169.

[21] Appl. No.: 394,930

[22] Filed: Feb. 24, 1995

Related U.S. Application Data

[63] Continuation of Ser. No. 151,707, Nov. 12, 1993, abandoned, which is a continuation of Ser. No. 883,511, May 15, 1992, Pat. No. 5,284,169.

[51] Int. Cl.$^6$ ............................................. A61C 15/00
[52] U.S. Cl. ............................................. 132/321; 132/329
[58] Field of Search ..................................... 132/321, 329

[56] References Cited

U.S. PATENT DOCUMENTS

| | | |
|---|---|---|
| 174,619 | 3/1876 | Clark, Jr. . |
| 660,943 | 10/1900 | Bauermeister . |
| 2,667,443 | 1/1954 | Ashton . |
| 2,700,636 | 1/1955 | Ashton . |
| 2,748,781 | 6/1956 | Collat . |
| 3,412,192 | 11/1968 | Clapson . |
| 3,492,131 | 1/1970 | Schlatter . |
| 3,615,671 | 10/1971 | Shoaf et al. . |
| 3,642,491 | 2/1972 | Schlatter . |
| 3,699,979 | 10/1972 | Muhler et al. . |
| 3,771,536 | 11/1973 | Dragan . |
| 3,789,858 | 2/1974 | Pesce ........................... 132/321 |
| 3,800,046 | 3/1974 | Schlatter . |
| 3,830,246 | 8/1974 | Gillings . |
| 3,837,351 | 9/1974 | Thornton . |
| 3,838,702 | 10/1974 | Standish et al. . |
| 3,896,824 | 7/1975 | Thornton ........................... 132/321 |
| 3,897,795 | 8/1975 | Engle . |
| 3,943,949 | 3/1976 | Ashton et al. . |
| 4,008,727 | 2/1977 | Thornton . |
| 4,029,113 | 6/1977 | Guyton . |

(List continued on next page.)

FOREIGN PATENT DOCUMENTS

| | | |
|---|---|---|
| 0080440 | 6/1983 | European Pat. Off. . |
| 0335466 | 10/1989 | European Pat. Off. . |
| 2216803 | 10/1989 | United Kingdom . |

*Primary Examiner*—Todd E. Manahan
*Attorney, Agent, or Firm*—Oblon, Spivak, McClelland, Maier & Neustadt

[57] ABSTRACT

A dental floss brush made from a reverse twisted, high tenacity nylon yarn comprising at least two thread sections having diameters, in their relaxed state, of at least 2.5 min. The thread sections are separated by a floss brush section integral therewith having a diameter of from up to 4 mm in its relaxed state and a diameter of from 1.7 to 3.0 mm under a tension of 0.05N. The brush floss has a breaking strength of at least 5N. The floss brush section can be coated with a low melting wax composition, optimally a polyethylene glycol ester of beeswax alone or in combination with a flavoring oil, silicone oil lubricant or mixtures thereof. This product is made by coating a reverse twisted, high tenacity nylon yarn with a solution of polymer in a volatile solvent, the polymer being selected from the group consisting of nylon, polyurethane and mixtures thereof. Then the solvent is selectively vaporized from thread portions of the yarn while preventing significant vaporization of solvent from brush portions of the yarn, while the yarn is maintained under a tension of from 0.15 to 1N. The brush portions of the yarn are steam treated while the yarn is under a tension of approximately zero until the brush portions of the yarn have regained at least 100 percent of the diameter of the uncoated, relaxed yarn. Residual solvent is then removed from the brush portions of the yarn while the yarn is under a tension of approximately zero.

15 Claims, 2 Drawing Sheets

U.S. PATENT DOCUMENTS

| | | |
|---|---|---|
| 4,033,365 | 7/1977 | Klepak et al. . |
| 4,071,615 | 1/1978 | Barth . |
| 4,142,538 | 3/1979 | Thornton . |
| 4,291,017 | 9/1981 | Beierle et al. . |
| 4,414,990 | 11/1983 | Yost .................................. 132/321 |
| 4,548,219 | 11/1985 | Newman et al. . |
| 4,627,975 | 12/1986 | Lynch . |
| 4,638,823 | 1/1987 | Newman et al. . |
| 4,817,643 | 4/1989 | Olson . |
| 4,911,927 | 3/1990 | Hill et al. . |
| 4,952,392 | 8/1990 | Thame . |
| 4,974,615 | 12/1990 | Doundoulakis ................ 132/321 |
| 4,986,288 | 1/1991 | Kent et al. . |
| 4,996,056 | 2/1991 | Blass . |
| 4,998,978 | 3/1991 | Varum . |
| 5,033,488 | 7/1991 | Curtis et al. .................. 132/321 |
| 5,063,948 | 11/1991 | Lloyd ............................ 132/321 |

THIN FLOSS BRUSH

This application is a continuation of application Ser. No. 08/151,707, filed on Nov. 12, 1993, now abandoned, which is in turn a continuation of application Ser. No. 07/883,511 filed May 15, 1992, now U.S. Pat. No. 5,284, 169.

FIELD OF THE INVENTION

This invention relates to an improved thin floss brush product and to a novel process for its manufacture. In particular this invention is directed to an improved floss brush made of a textured, high tenacity nylon yarn which provides the scraping functions of a floss under high tension and the brushing functions of a yarn under low tension.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

To improve the effectiveness and convenience of dental flosses, dental flosses combining a thin "floss" portion and a thickened "brush" portion, together with a threader have been developed. The brush portion, when drawn between tooth surfaces, has been found to provide an improved cleaning action which removes materials left by the floss portion, when used alone. The combination provides a substantially superior cleaning action. Such a device is described in U.S. Pat. No. 4,008,727, for example. The complexity of this product requires that each floss segment be individually manufactured and that the product be packaged as bundles of the individual, separate floss articles.

A continuous yarn having brush segments separated by thinner segments is disclosed in U.S. Pat. Nos. 4,008,727 and 4,142,538. However, products formed using conventional textured nylon yarns and previously developed manufacturing processes were not satisfactory. Manufacture of brush floss products of this type involves applying a polymer solution to the yarn. The solvent is then selectively evaporated from the thinned segment portion while avoiding solvent evaporation from the brush portion, the yarn being maintained under high tension during this procedure. The solvent in the brush portion is then removed while the yarn is relaxed, that is, under low or no tension. Thin yarn products of most texturizing processes were found to be too weak to be placed under the high tension required for forming the desired thin section. Furthermore, the polymer impregnated brush portion did not regain its original bulk and texture when the tension was relaxed prior to solvent removal from the brush portion.

Attractive and pleasant flavors and flavor odors have been provided in dental products including dental flosses to impart a flavor to the flosses and encourage their regular use. These have been applied in the form of flavoring oils to the surface of floss or wax coating on the floss, or dispersed in wax coatings applied to the floss. In a process described in copending, commonly assigned application Ser. No. 07/809,625 filed Dec. 17, 1991, flavoring oils are applied to floss in a low-melting wax composition containing a mixture of high and low melting point polyethylene glycols, the low melting characteristic of the wax retaining the flavoring oils without significant loss through evaporation or from oxidation. Application of these compositions to a floss brush was found to be unsatisfactory because they clogged and matted the yarn, reducing its value as a brush cleaning article.

OBJECTS AND SUMMARY OF THE INVENTION

It is one object of this invention to provide an improved floss brush which can be spooled and dispensed as a continuous brush/thread from a traditional floss dispenser.

It is another object of this invention to provide a polymer coated floss brush made from a textured yarn which retains substantially all of the bulk and thickness of the original, uncoated, relaxed yarn.

It is still a further object of this invention to provide a floss brush with a high flavor content.

The dental floss brush of this invention is made from a reverse twisted, high tenacity nylon yarn. It comprises at least two thread sections having diameters, in their relaxed state, of less than 2.5 mm preferably less than 1.35 mm. The thread sections are separated by a floss brush section integral therewith of yarn having a diameter of from 2 to 4 mm, preferably from 2.4 to 3.5 mm, in its relaxed state and a diameter of from 1.7 to 3.0 mm under a tension of 0.05N (newtons). The brush floss has a breaking strength of at least at least 5N and preferably above 20N. Optimally, the yarn has a breaking strength of at least 35N; the thread sections have diameters, in their relaxed state, of less than 50 percent of the diameter of relaxed, uncoated yarn from which they were formed; the floss brush has, in its relaxed state, at least 100 and preferably at least 220 percent of the original diameter of relaxed, uncoated yarn from which it was formed; and each floss brush section has a diameter under a tension of 0.05N of at least 60 percent, preferably above 75 percent, and optimally above 150 percent of the relaxed uncoated yarn from which it was formed.

In one embodiment, the floss brush is coated with a low melting wax composition, optimally a polyethylene glycol ester of beeswax, alone or in combination with a flavoring oil, silicone oil lubricant or mixtures thereof.

In summary, one process of this invention is a process for manufacturing a continuous length of dental floss brush comprising alternating sequences of thread portions and floss brush portions integral therewith. The process comprises the steps of a) coating a reverse twisted high tenacity nylon yarn with a solution of polymer in a volatile solvent, the polymer being selected from the group consisting of nylon, polyurethane and mixtures thereof;

b) selectively vaporizing solvent from thread portions of the yarn while preventing significant vaporization of solvent from brush portions of the yarn, while the yarn is maintained under a tension of from 0.15 to 1N;

c) steam treating the brush portions of the yarn while the yarn is under a tension of approximately zero until the brush portions of the yarn have regained at least 100 percent and preferably at least 220 percent of the diameter of the uncoated, relaxed yarn; and d) removing residual solvent from the brush portions of the yarn while the yarn is under a tension of approximately zero.

Preferably, the solution of polymer comprises from 5 to 15 wt.% polyurethane and from 5 to 15 wt.% nylon. Optimally, the solvent is an aqueous ethanol solution containing at least 57 wt.% ethanol. Optimally, the steam treatment is conducted at a temperature of from 80° to 105° C. The solvent can be selectively vaporized from thread portions of the yarn by exposing the thread portions to heat while shielding the brush portions adjacent thereto with heat insulators.

Optionally, the process includes the additional steps of coating the threads of the brush portion of the product of step (d) with low melting wax without clogging the openings thereof. This can be effected by applying the coating as a liquid wax at a temperature of from above about 50° up to 80° C., removing excess portions of the wax, and cooling the coated brush portions to a temperature below 50° C. The low melting wax, preferably a polyethylene glycol ester of beeswax, can be used alone or in combination with a flavoring agent, silicone oil lubricant or mixtures thereof.

The process of this invention for restoring the bulk of stretched yarn coated with a polymer solution following relaxation of tension thereon comprises the step of treating the yarn with steam while the yarn is under a tension of approximately zero until the brush portions of the yarn have regained at least 100 and preferably 220 percent of the diameter of the uncoated, relaxed yarn.

The process of this invention for producing a wax coated nylon yarn with unclogged openings comprising coating the yarn with a polyethylene glycol ester of beeswax liquid at a temperature of from 50° to 80° C., removing excess portions of the liquid, and cooling the coated yarn to a temperature below 50° C. The liquid can optionally contain a flavoring oil, silicone oil lubricant, or mixtures thereof.

The products of these processes are also aspects of this invention.

DETAILED DESCRIPTION OF THE INVENTION

The elongate teeth cleaning article of this invention provides the combined functions of an interproximal brush and floss. In the representation shown in FIG. 1, the polymer coated thin floss brush 2 comprises a brush portion 4 positioned between terminal thread portions 6 and 8 integral therewith. The brush is relaxed and yarn-like, suitable for cleaning between the teeth in a brushing action, pulling the floss back and forward across tooth and gingiva surfaces. The cavities in the brush surface capture and remove food, bacteria and other materials on the tooth and gum surfaces. Under tension, the brush portion stretches to become a thread, suitable for the upward and downward scraping motion along the opposed tooth surfaces and facilitates easier insertion between interstitial spaces. When relaxed, the brush portion returns to the yarn-like extended configuration.

Figure 1:
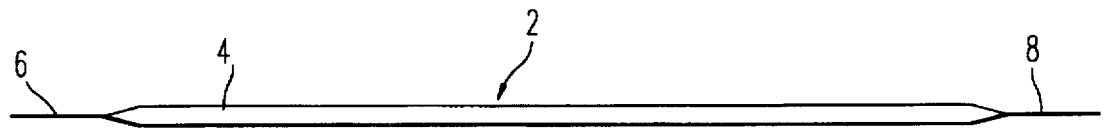
FIG. 1 is a representation of the relaxed dental floss brush of this invention.
Figure 2:
FIG. 2 is a representation of a continuous length of relaxed, connected dental floss brushes of this invention.

The thin floss brush 2 is manufactured in a continuous length of alternating thread and brush portions, a portion of which is shown in FIG. 2. By severing the thread portion 10 separating a terminal thread and brush portion 12, a length of floss corresponding to FIG. 1 is obtained. This continuous length of floss is suitable for dispensing from a spool in a conventional floss dispenser.

Figure 3:
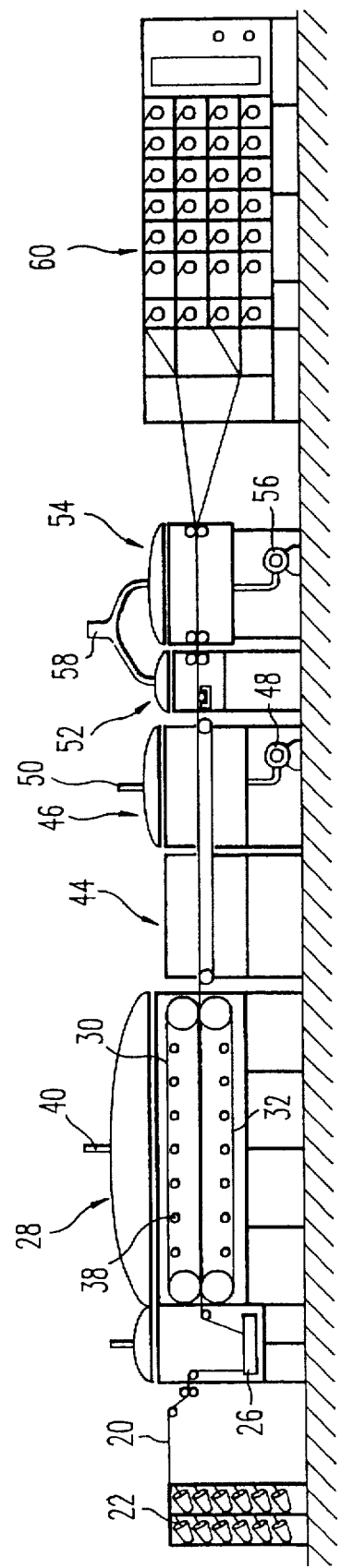
FIG. 3 is a schematic representation of the system for producing a continuous length of connected dental floss brushes of this invention.

FIG. 3 is a schematic representation of the system for producing a continuous length of connected dental floss brushes of this invention. The article is manufactured by processing a yarn, preferably a high tenacity nylon yarn, with a polymer coating, evaporating solvent from the thread portions under tension, steam treating the relaxed yarn, removing excess solvent and evaporating residual solvent, and optionally coating the yarn with a low melting, non-clogging wax coating followed by removing excess coating and cooling the yarn. The product is then collected on reels (spools or cones) which are further processed through a packaging operation to provide the finished output product.

Yarn 20 is drawn from yarn packages (spools or cones) which is mounted on a creel 22. Yarn 20 is pulled through the coating bath 26. In coating bath 26, a polymer solution in a volatile solvent is applied to the yarn while the tension is increased, effecting liquid penetration of the yarn while avoiding excessive liquid pickup. Any excess coating solution is removed by conventional squeeze rollers. The coated yarn is then transported through a device that applies a dye to a selected segment such as the thread section.

Figure 4:
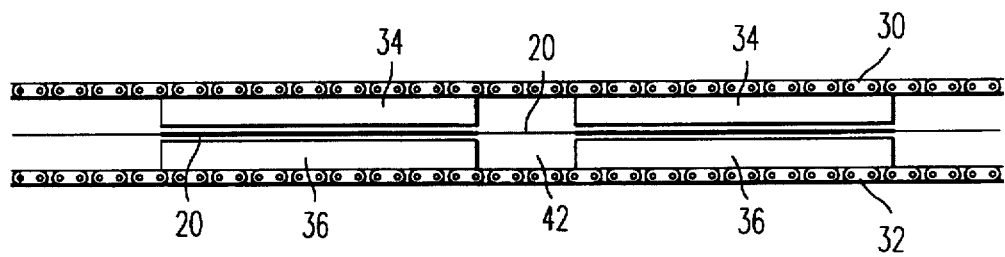
FIG. 4 is a schematic representation of a portion of the drier and heater assembly shown in FIG. 3.

The coated, dyed yarn is then pulled into a chain driven drying chamber 28. Referring to FIGS. 3 and 4, this system comprises opposed moving chains 30 and 32, the opposing faces of each moving chain having respective insulating pads 34 and 36. The upper chain sections include infrared heaters housed in a stainless steel vestibule. The lower chain section includes an air exhaust vestibule. The combination of the forced convection and radiant heat evaporates solvent which is removed from the driving chamber through the air exhaust vestibule 40. The portions of the yarn suspended between and shielded by adjacent insulating pad pairs in heating zones 42 are exposed to the heat, and the exposed coating is completely dried and hardened (the solvent is substantially vaporized) by the time it reaches the exit of the drying chamber. The exposed, dried portions retain the thin configuration formed under tension, producing the thread portion. The portions of the yarn held between the insulating pads 34 and 36 are protected from the heat and experience little or no solvent loss during the period of high tension. The infrared heaters are designed and arranged to provide drying temperatures of from about 70° to 160° C.

The yarn is then passed under relaxed conditions (i.e., low or zero tension) into a steam treatment chamber 44. When the yarn tension is relaxed after emerging from the heater section 28, these undried portions partially contract to a partially bulked configuration. In steam chamber 44, the brush portions are exposed to substantially saturated steam having a temperature within the range of from 80° to 105° C. until the brush portions almost completely contract and substantially regain the original puffiness and bulked condition of the initial uncoated, relaxed yarn. This is usually achieved by a treatment of 3 seconds and longer, depending upon the nature and level of coating.

The rebulked, steam-treated floss is then passed into roller driven drying chamber 46. The residual liquid (solvent and water) is evaporated by conduction and convection heat transfer using heated air having a temperature within the range of from 150° to 200° C. and a flow rate of 150 to 300 cfm. Air is supplied through manifold 50 and vapors are removed through exhaust system 48.

The continuous length of floss brush can be collected on reels as an unwaxed floss product at this stage.

Optionally, for producing a waxed floss brush, the solvent-free floss is passed through a wax coating bath 52 where a low melting wax coating is applied at an elevated temperature. The excess wax coating is removed by passing the floss brush between squeeze rollers, and the continuous length of floss brush is passed into the refrigeration or cooling station 54. Passing through a gas stream produced by blower 56, solvents are evaporated and the vapors removed through exhaust manifold 58. The wax coated product is then collected on reels (spools or cones) in the collecting station 60.

The floss brush is then rewound from the spools or cones onto conventional individual dispenser spools.

Most textured nylon yarns were found to lack the tensile strength required for this process. The products of most bulking processes lack the aesthetic appeal required for this product, i.e., wild strands, broken filaments, etc. False twist texturizing provides the most satisfactory aesthetic appearance. For making a thin floss brush product, use of yarn having a lower decitex is required without sacrificing strength.

False twisting gave an acceptable aesthetic product, but strength was found to be limiting. During texturizing, the yarn is subjected to extreme heat, reducing its strength. For yarns prepared by twisting together an uneven number of ends (such as five 2×2×1), often one end failed under tension, reducing the overall strength of the yarn. We found that by controlling the heat to avoid damaging extremes, a false twisted product having the required strength could be obtained.

The steaming process increased bulk of the yarn, yielding a product which slips easily between teeth under tension and which bulks up to be used either as a floss, cleaning by scraping up and down, or by linear movement as a brush. The bulked portion is easier on the gums. The product can accept liquid or solid flavoring materials because of its open mesh structure and increased surface area over regular floss. This provides a product with a more lasting flavor and increased customer appeal.

Reverse or false twisted, high tenacity nylon yarn having a breaking strength of at least above 5N, preferably above 20N and optimally above 35N was found to be satisfactory. These yarns are formed by first texturizing a high tenacity nylon yarn using a conventional pin-twisting process, using only sufficient heat required for the texturizing and avoiding temperatures which will significantly damage the yarn and its filaments and reduce their strength. Left and right pin-twisted strands are then combined to form the final reverse-twisted, textured yarn product. A suitable yarn is available from Chapman Fraser & Co. Ltd. Thurmaston, Leicester, England.

The polymer solution applied in coating bath 26 can be a solution or emulsion of a nylon, polyurethane or mixtures thereof. Suitable nylon solutions in lower alkanols of the types conventionally used in coating dental flosses are suitable. An example is the GENTAL™ alkanolic nylon solutions (General Plastics Corporation, Bloomfield, N.J.). Preferred polyurethanes are water dispersible urethanes such as the anionic colloidal urethane elastomer dispersions sold under the tradename SPENSOL® polyurethane dispersions (Spencer-Kellog Products). Optimally, the coating solution or emulsion is a mixture of from 5 to 15 percent of alkanol-soluble nylon and from 5 to 15 percent water-dispersible polyurethane in a mixed water/alkanol solution such as a water/ethanol solution such as a mixture of 75 wt.% of GENTAL™ A151A alkanolic nylon solution and 25 wt % of SPENSOL®L54 aqueous polyurethane dispersion.

Application of conventional microcrystalline waxes or polyethylene glycol waxes to nylon yarns clog the spaces of the yarn and make it ineffective for use as a brush. We have discovered, however, that heated liquid polyethylene glycol esters of beeswax can be use to coat such yarns, and if the excess is removed before cooling, only the individual filaments of the yarn are coated and most of the original yarn texture and cleaning ability is retained.

The heated polyethylene glycol esters of beeswax have a low melting temperature, usually within the range of from 65° to 70° C., and are mutually soluble with flavor oils. They therefore provide a suitable vehicle for applying flavoring to the floss brush. They also function as emulsifiers and surfactants and can be combined with alkanolic or aqueous solutions of sweeteners such as saccharine, cyclamates or xylitol and with lubricants such as silicone oils. Preferred low melting wax coating compositions are esters of polyethylene glycols having an average molecular weight of 300 and beeswax. Preferred coating compositions containing liquid flavors (A) and a mixture of liquid and encapsulated flavors (B) are shown in the following table.

| FLAVORED WAX COATING COMPOSITION | | |
|---|---|---|
| | Amount, wt. % | |
| Component | A | B |
| Polyethylene glycol ester of beeswax[a] | 36.0 | 30.5 |
| Silicone oil lubricant[b] | 27.0 | 25.0 |
| Mint flavor[c] | 34.0 | 26.0 |
| Spearmint cap.[d] | | 4.0 |
| Peppermint cap.[e] | | 12.0 |
| Saccharin | 0.6 | 0.5 |
| Ethanol, 96% | 2.4 | 2.0 |

[a]ESTOL E03BW 3751, Unichema International
[b]DOW CORNING 200 Fluid, 350 cSt
[c]Noville Fragrance #62082
[d]Encapsulated Spearmint Borden# 13587
[e]Encapsulated Peppermint Borden# 137422

Although preferred embodiments of the subject invention have been described in some detail, it is understood that obvious variations can be made without departing from the spirit and the scope of the invention as defined by the appended claims.

The invention claimed is:

1. A continuous length of dental floss comprising alternating sequences of thread portions and floss brush portions integral therewith as manufactured by a process comprising the steps of a) coating a reverse twisted high tenacity nylon yarn with a solution of polymer in a volatile solvent, the polymer being selected from the group consisting of nylon, polyurethane and mixtures thereof;

b) selectively vaporizing solvent from thread portions of the yarn and preventing significant vaporization of solvent from brush portions of the yarn while the yarn is maintained under a tension of at least 0.15N;

c) bulking up the brush portions by exposing the brush portions of the yarn to steam while the yarn is under a tension of approximately zero; and d) removing residual solvent from the brush portions of the yarn while the yarn is under a tension of approximately zero.

2. A continuous length of dental floss of claim 1 wherein the dental floss is made from a reverse twisted, high tenacity nylon yarn comprising at least two thread sections having diameters, in their relaxed state, of less than 2.5 mm, the thread sections being separated by a floss brush section integral therewith of yarn having a diameter of up to 4 mm in its relaxed state, and a reduced diameter when placed under tension, the floss brush having a breaking strength of at least 5N.

3. A continuous length of dental floss of claim 1 wherein the reverse twisted high tenacity nylon yarn has a breaking strength of at least 20N.

4. A continuous length of dental floss of claim 1 wherein the thread sections have diameters, in their relaxed state, of less than 50 percent of the diameter of relaxed, uncoated yarn from which they were formed.

5. A continuous length of dental floss of claim 1 wherein each floss brush section has a diameter under a tension of 0.05N of at least 60 percent of relaxed uncoated yarn from which it was formed.

6. A continuous length of dental floss of claim 1 wherein the floss brush is coated with a low melting wax composition.

7. A continuous length of dental floss of claim 6 wherein the wax composition consists essentially of polyethylene glycol ester of beeswax.

8. A continuous length of dental floss of claim 6 wherein the wax composition is mixed with a flavoring oil, silicone oil lubricant or mixtures thereof.

9. A continuous length of dental floss of claim 1 wherein the solution of polymer in the process contains from 5 to 15 wt. % polyurethane composition and from 5 to 15 wt.% nylon composition.

10. A continuous length of dental floss of claim 1 wherein the solvent in the process is an aqueous ethanol solution containing at least 57 wt.% ethanol.

11. A continuous length of dental floss of claim 1 wherein the steam in the process has a temperature of from 80° to 105° C.

12. A continuous length of dental floss of claim 1 wherein the solvent is selectively vaporized from thread portions of the yarn by exposing the thread portions to heat while shielding the brush portions adjacent thereto with heat insulators.

13. A continuous length of dental floss of claim 1 wherein the process includes the additional steps of coating the threads of the brush portion of the product of step (d) with a low melting wax without permanently clogging the openings thereof.

14. A continuous length of dental floss of claim 13 wherein the low melting wax is a polyethylene glycol ester of beeswax having a temperature of from above 50° up to 80° C., excess portions of the wax is removed, and the coated brush portions are cooled to a temperature below 50° C.

15. A continuous length of dental floss of claim 13 wherein the low melting wax is mixed with a silicone oil lubricant, flavoring oil or mixtures thereof.

* * * * *